United States Patent [19]
Barrett et al.

[11] Patent Number: 6,010,894
[45] Date of Patent: Jan. 4, 2000

[54] METHOD OF SCREENING FOR ATTENUATING VIRUSES

[75] Inventors: Alan Barrett; Haolin Ni, both of Galveston, Tex.; Kate Ryman, Carrboro, N.C.

[73] Assignee: Research Development Foundation, Carson City, Nev.

[21] Appl. No.: 08/874,272

[22] Filed: Jun. 13, 1997

[51] Int. Cl.[7] .................................................. L12N 5/00
[52] U.S. Cl. .................. 435/235.1; 435/236; 435/237; 435/5; 424/93.6; 424/218.1
[58] Field of Search .................. 435/236, 235.1, 435/237, 5; 424/93.6, 218.1

[56] References Cited

PUBLICATIONS

Cao et al. Journal of General Virology. vol. 76(11). pp. 2757–2764, 1995.

*Primary Examiner*—Leon B. Lankford, Jr.
*Attorney, Agent, or Firm*—Benjamin Aaron Adler

[57] ABSTRACT

The present invention provides a method of selecting virus vaccine candidates by selecting virus variants that do not bind to brain membrane receptor preparations, comprising the steps of: (a) preparing a brain membrane receptor preparation; (b) mixing an amount of a virus of interest with an amount of said membrane receptor preparation containing excess membrane receptors to form a virus-membrane receptor preparation suspension; (c) centrifuging said suspension to form a supernatant; (d) determining residual virus infectivity in said supernatant; and (e) isolating individual membrane receptor preparation binding-resistant virus variants which are useful as virus vaccine candidates.

8 Claims, 2 Drawing Sheets

SA14: virulent parent isolated from mosquitos in China.

BHK21

SA14/JAP mouse brain 11 x passages in newborn mice,
100 x passages in PHK cell culture,
3 x plaque purification.

SA14/USA    Clone 12-1-7    ultraviolet irradiation

3 PDK passages    First attenuated variant 12 passages

SA14/CDC    SA14-5-3    SA14-2-8

7 passages

SA14-14-2/PHK

9 PDK passages

SA14-14-2/PDK

SA14: virulent parent isolated from mosquitos in China.

SA14/JAP ←—BHK21— mouse brain 11 x passages in newborn mice,
100 x passages in PHK cell culture,
3 x plaque purification.

SA14/USA

Clone 12-1-7 ——ultraviolet irradiation——
First attenuated variant

3 PDK passages 12 passages

SA14/CDC    SA14-5-3    SA14-2-8

7 passages

SA14-14-2/PHK

9 PDK passages

SA14-14-2/PDK

FIG. 1

METHOD OF SCREENING FOR ATTENUATING VIRUSES

BACKGROUND OF THE INVENTION

1. Field of the Invention

The present invention relates generally to the fields of virology, immunology and protein chemistry. More specifically, the present invention relates to a novel method of attenuating viruses.

2. Description of the Related Art

Vaccination is the best approach to reducing mortality and morbidity of humans caused by infectious diseases. Vaccines have made significant contributions to the eradication or control of several major infectious diseases in the world, such as smallpox, yellow fever, poliomyelitis and measles. In particular, live attenuated vaccines have been successful due to stimulation of different arms of the host immune response. These live vaccines are natural virus variants derived by passaging virus in abnormal hosts, e.g. yellow fever 17D virus in chicken tissue (Monath, 1990). However, this method is empirical, not cost-efficient, and takes a long time to develop a useful vaccine that can be administered to humans.

A virus can not infect a susceptible cell unless its viral attachment protein can bind to a molecule on the cell surface which serves as receptor for the particular virus. The expression of the receptor on specific cells or tissues in the whole host is a major determinant of route of virus entry into the host, the pattern of virus spread in the host and resulting pathogenesis (Marsh and Helenius, 1989; Lentz, 1989; Dimmock and Primrose, 1995). There are many factors determining host range and tissue tropism of viruses, including the nature, number and distribution of host cell receptor sites, which may be multivalent and consist of several receptor units (Paulson, 1985; Mims, 1986).

Japanese encephalitis (JE) is a disease caused by Japanese encephalitis virus, a mosquito-borne flavivirus which is epidemic throughout Asian countries (Huang, 1982) and the most common epidemic virus encephalitis in the world. The virus has a tissue tropism for the brain, in particular neurons. Japanese encephalitis virus belongs to genus flavivirus of the family Flaviviridae (Westaway et al., 1985). The genome of the virus consists of one single-stranded, positive sense RNA which is 10986 nucleotides in length and contains one long open reading frame that encodes three structural proteins at the 5' end (capsid (C), membrane (M) and envelope (E) proteins) and seven non-structural proteins (NS1, NS2A, NS2B, NS3, NS4A, NS4B and NS5) at the 3' end. The virus causes a neurological disease with a mortality rate of up to 50% and as many as 70% of survivors may develop neurological sequelae. There is no therapy to prevent the disease. Consequently, vaccines are used to control the disease (1). Attempts to generate live attenuated vaccines have proven difficult due to the neurotropism of the virus and the potential of reversion to virulence. Currently, little is known about the molecular basis of attenuation and virulence of Japanese encephalitis virus.

The prior art is deficient in the lack of effective means of attenuating viruses. The present invention fulfills this longstanding need and desire in the art.

SUMMARY OF THE INVENTION

Currently, the molecular basis of attenuation and virulence of Japanese encephalitis (JE) virus is not fully understood. Attenuation and virulence has been examined using two systems: the first system involves the process of attenuation of wild-type strain SA14 to generate live attenuated vaccines by passage in primary hamster kidney cell culture. The genome of SA14 differs from its four vaccine derivatives at only seven common amino acids (E-138, E-176, E 315, E-439, NS2B-63, NS3-105 and NS4B-106). The second system involves analysis of wild type strain P3 which is the most virulent strain identified to date. Comparison of the genome of strain P3 with other wild-type strains has enabled identification of 16 unique amino acids, including 9 in the envelope (E) protein, involved in the virulent phenotype of strain P3. Mouse brain membrane receptor preparation binding-resistant variants indicate that E-306 and E-408 are involved in receptor binding. Overall, studies to date indicate that the E protein is a key determinant of the mouse attenuated or virulent phenotype of Japanese encephalitis virus.

Three variants of Japanese encephalitis virus strain P3 were selected for resistance to binding to mouse brain membrane receptor preparations (MRP). These $MRP^R$ variants were significantly attenuated in mice for both neuroinvasiveness (>200 fold) and neurovirulence (>1000 fold) compared to their parent virus.

All attenuated mouse brain $MRP^R$ variants replicated in sera of mice following either intracerebral (i.c.) or intraperitoneal (i.p.) inoculation whereas replication was detected in brains of mice following i.c. inoculation. Two common amino acid mutations were found in the envelope (E) protein genes of all mouse brain $MRP^R$ variants at residues E-306 and E-408 of the E protein compared to P3 virus grown in mosquito C6–36 cells or purified and amplified in monkey kidney Vero cells. These amino acids are putatively responsible for attenuation due to alteration in binding of Japanese encephalitis virus to its cell receptor in mouse brain. Generation of Japanese encephalitis human brain $MRP^R$ variants resulted in viruses that were attenuated 5,000,000-fold for mouse neurovirulence. Similarly, yellow fever monkey brain $MRP^R$ variants were attenuated 8,000-fold for neurovirulence in mice and Langate virus mouse brain $MRP^R$ variants were attenuated up to 16,000-fold for mouse neurovirulence. The methodology developed herein has general applicability to attenuation of virulence of viruses and to identify agents that block amino acids in viral attachment protein(s) that interact with cell receptors.

In one embodiment of the present invention, there is provided a method of selecting virus vaccine candidates by selecting virus variants that do not bind to brain membrane receptor preparations, comprising the steps of: (a) preparing a brain membrane receptor preparation; (b) mixing an amount of a virus of interest with an amount of said membrane receptor preparation containing excess membrane receptors to form a virus-membrane receptor preparation suspension; (c) centrifuging said suspension to form a supernatant; (d) determining residual virus infectivity in said supernatant; and (e) isolating individual membrane receptor preparation binding-resistant virus variants which are useful as virus vaccine candidates.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the passage history of the SA14-derived vaccine viruses.

FIG. 2 shows the model of structure of the ectodomain of the E protein (modified from 17).

DETAILED DESCRIPTION OF THE INVENTION

Figure 2A:
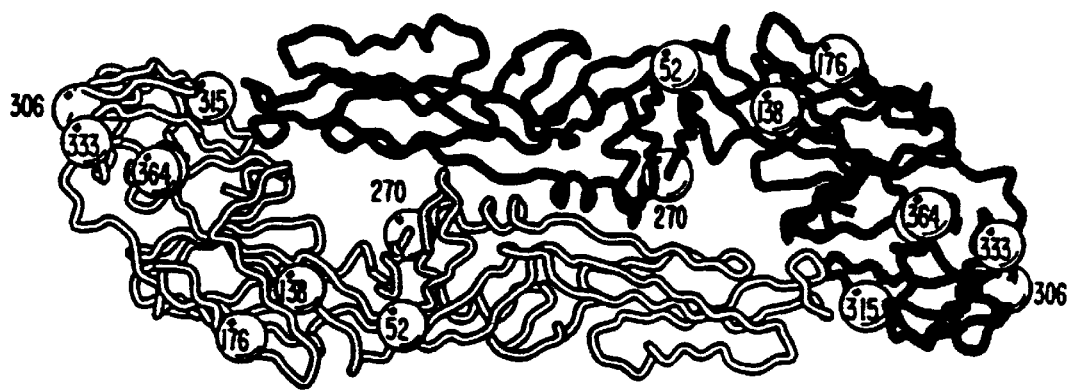
FIG. 2A: top view.
Figure 2B:
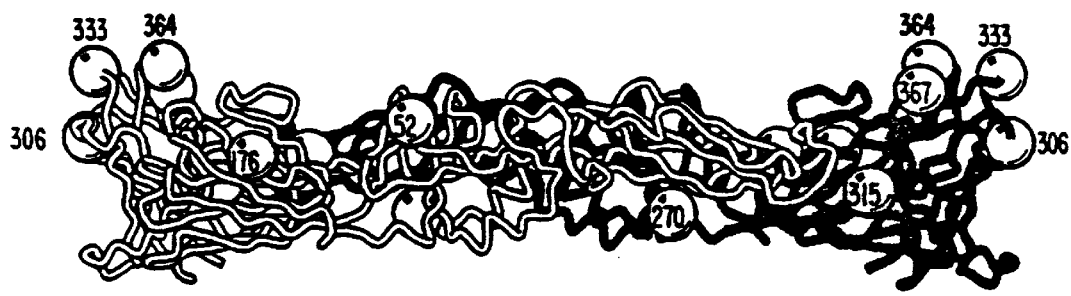
FIG. 2B: side view.

In the present invention, a highly neurovirulent flavivirus, Japanese encephalitis virus, has been used as a model system to investigate the viral attachment protein-cell receptor interaction. A novel methodology has been established to select potential virus vaccine candidates.

One object of the present invention is the selection of Japanese encephalitis virus variants that do not bind to mouse brain membrane receptor preparations ($MRP^R$).

Another object of the present invention is the evaluation of attenuation of neurovirulence and neuroinvasiveness of the $MRP^R$ variants in mice.

A further object of the present invention is the analysis of the genetic mutation(s) responsible for attenuation of virulence of the $MRP^R$ variants. Identification of amino acids in the viral attachment protein that bind to a cell receptor is a desirable route to generation of live attenuated vaccines and understanding the molecular basis of cell/tissue tropism of viruses.

The present invention is directed to a method of selecting virus vaccine candidates by selecting virus variants that do not bind to brain membrane receptor preparations, comprising the steps of: (a) preparing a brain membrane receptor preparation; (b) mixing an amount of a virus of interest with an amount of said membrane receptor preparation containing excess membrane receptors to form a virus-membrane receptor preparation suspension; (c) centrifuging said suspension to form a supernatant; (d) determining residual virus infectivity in said supernatant; and (e) isolating individual membrane receptor preparation binding-resistant virus variants which are useful as virus vaccine candidates. Preferably, said brain membranes are selected from the group consisting of mouse brain membranes and human brain membranes. When prepared according to the methods described herein, said brain membrane receptor preparation has a protein concentration of about 20–40 mg wet brain per ml. Preferably, for Japanese encephalitis the residual virus infectivity in said supernatant is determined by infecting a Vero cell monolayer and counting plaques produced. Preferably, after said the individual membrane receptor preparation binding-resistant variant plaques are isolated, the viruses are amplified. Variants generated by the methods described herein are incubated with fresh brain membrane receptor preparations and a lack of binding of the variants to fresh brain membrane receptor preparations confirm that the variants are true variants. Most preferably, the variants are attenuated for neuroinvasiveness and neurovirulence. Although virtually, any virus may be attenuated using the methods of the present invention, representative viruses include yellow fever, dengue-4, and langat.

Given the techniques disclosed by the instant specification, a person having ordinary skill in this are would be able to design anti-viral compounds based on identification of amino acids responsible to the cell receptor sites on a three dimensional structure of the viral attachment protein that binds a receptor.

Given the techniques disclosed by the instant specification, a person having ordinary skill in this are would be able to design sequential mutants by generating a $MRP^R$ mutant using one tissue followed by sequential selection using a $MRP^R$ mutant from a second tissue. In such a way a variant can be designed to which is attentuated for multiple tissues and this would be desirable since some viruses demonstrate disease potential in different tissues.

The following examples are given for the purpose of illustrating various embodiments of the invention and are not meant to limit the present invention in any fashion.

EXAMPLE 1

Molecular determinants of virulence of JE virus

As with most viruses, Japanese encephalitis virus demonstrates strain variation. Strain P3 is recognized as being, a highly virulent strain whereas strains JaOArS982 and Nakayama are of intermediate virulence, and SA14 is of low virulence (TABLE I).

TABLE I

Comparison of the Virulence of Wild-Type JE Virus Strains in Weanling Mice Following Different Routes of Inoculation

| | Lethality ($pfu/LD_{50}$) | | |
|---|---|---|---|
| Virus | Intracerebral | Intranasal | Intraperitoneal |
| P3 | 0.0001 | NT | 50 |
| Nakayama | 0.1 | 800 | 10,000 |
| JaOArS982 | 0.1 | NT | 3,000,000 |
| SA14/USA | 2 | >5,000,000 | >5,000,000 |

NT: Not tested

EXAMPLE 2

Envelope protein

The E protein is the major structural protein of the virus and is thought to encode the virus attachment protein, i.e., the viral protein that interacts with the cell receptor. Since four of the seven SA14 vaccine amino acid substitutions are in the E protein, attenuation may be, in part, due to altered cell tropism of the vaccine strains. This is supported by immunohistochemical studies which show a very small number of neurons in mouse brain contain SA14-14-2 viral antigen, and none of the cytopathological features seen following infection by wild-type parental strain SA14 (9).

Studies with anti-Japanese encephalitis virus monoclonal antibody neutralization-resistant (MAbR) variants show that mutations at E-52+E-364+E-367 (10), or E-270, or E-333 (11) all attenuate mouse neuroinvasiveness, but not neurovirulence. Examination of monoclonal antibody neutralization-resistant variants for other flaviviruses reveals that attenuated neuroinvasiveness (but not neurovirulence) maps to E-277 for Murray Valley encephalitis virus (12), E-308 (equivalent to E-305 for Japanese encephalitis virus) for louping ill virus (13), and E-384 (equivalent to E-384 for Japanese encephalitis virus) for central European tick-borne encephalitis (CE TBE) virus (14). Two other studies involving mutagenesis of Japanese encephalitis virus have shown that E-138 attenuates mouse neurovirulence and involves an identical substitution of Glu for Lys as seen with E-138 in the SA14 series of vaccines (15,16).

To illustrate the interaction of Japanese encephalitis virus with mouse brain in more detail, membrane receptor preparations were made from mouse brain using standard pharmacological techniques. The mouse brain membrane receptor preparations have been used to generate mouse brain membrane receptor preparations binding-resistant (MRP$^R$) variants. Three mouse brain membrane receptor preparation binding-resistant variants were generated from strain P3, shown not to bind to fresh mouse brain MRPs and were all attenuated for neuroinvasiveness and neurovirulence in mice (TABLE II). All three have the same two amino acid substitutions at E-306 and E408. Both residues are unique for strain P3 and the MRP$^R$ mutation induces a reversion to the residues found in other strains of Japanese encephalitis virus.

TABLE II

Mouse neurovirulence of parent JE P3 virus and the mouse brain: MRPR variants following intracerebral or intraperitoneal inoculation

|  |  | Route of inoculation | | |
| --- | --- | --- | --- | --- |
|  |  | intraperitoneal pfu/LD50 | intracerebral pfu/LD50 | AST ± SEM# |
| Parent | P3 | 50 | <0.0001 | 6.5 ± 0.3 |
| Mouse | MRP$^R$ I | >50,000 | 5.6 | 8.0 ± 1.2 |
| brain | MRP$^R$ II | >50,000 | 0.8 | 8.0 ± 1.2 |
| Variants | MRP$^R$ III | >50,000 | 10.0 | 8.6 ± 1.0 |

: AST ± SEM: Average survival time ± SEM which were carculated from mice inoculated with 10 pfu virus by i.c. route.

EXAMPLE 3

Viruses and cells

Wild-type Japanese encephalitis virus strains P3 virus was provided by Dr. Robert Shope of Yale Arbovirus Research Unit. Monkey kidney (Vero) cells and *Aedes albopictus* mosquito C6–36 cells were grown at 37° C. and 28° C., respectively, in Eagle's minimal essential medium (EMEM; Sigma) supplemented with 10% heat-inactivated fetal calf serum (FCS; Sigma), 2 mM L-glutamine (Sigma) and antibiotics.

EXAMPLE 4

Mouse brain membrane receptor preparation

Mouse brains were collected from the 3–4-week old female balb/C mice. The brain membrane receptor preparations (MRPs) were made based on the method described for neurotransmitter receptor binding assays (Middlemiss and Frozard, 1983). Briefly, the brains were rapidly dissected, weighed and homogenized in Tris buffer (50 mM, pH 7.6). The homogenate was centrifuged (35,600g for 10 minutes), the pellet resuspended in the same volume of Tris buffer and the process repeated twice. Between the second and third centrifugations, the homogenate was incubated at 37° C. for 10 minutes. The final pellet was resuspended in a volume of Tris buffer (50 mM pH 7.6) to give a final protein concentration of approximately 20–40 mg wet brain/ml and stored at −70° C.

EXAMPLE 5

Generation of virus mouse brain MRP escape (MRP$^R$) variants

Prior to use, aliquot(s) of frozen membrane receptor preparations and virus were removed from −70° C., rapidly thawed at 37° C. and kept on ice (4° C.). A 100 μl aliquot of virus was added to 900 μl of the mouse brain membrane receptor preparations containing excess membrane receptor (s), and vortexed. Control virus samples were prepared in the same way, but mixed with 900 μl of Tris buffer (50 mM Tris, pH 7.6) instead of membrane receptor preparation.

Samples were incubated at 37° C. for 30 minutes on a rotating stand. After incubation, the virus-membrane receptor preparation suspension and control virus-Tris buffer samples were centrifuged at 13,000 rpm for 10 minutes to remove the membrane material and bound virus. Residual virus infectivity in the supernatant was determined by infecting Vero cell monolayer and counting plaques produced after five days incubation at 37° C. The individual MRP$^R$ variant plaques were picked and amplified in Vero cells. The virus variants generated were investigated for binding to fresh membrane receptor preparations. Lack of binding of the virus variants to fresh mouse brain membrane receptor preparation confirmed that they were true MRP$^R$ variants.

EXAMPLE 6

Mouse pathogenicity studies

NIH-Swiss female outbred white mice, 3 to 4 weeks old were obtained from Harlan, Indianapolis, Ind. The mice were inoculated with either 20 μl of virus by the intracerebral route or 100 μl by the intraperitoneal (i.p.) route. Virulence studies involved eight mice per dose group, LD$_{50}$ and average survival time (AST) values were determined. Mice examined for infectivity were sacrificed at day two or day seven post i.c. or i.p. inoculation and the brains and sera were processed for infectivity titration by plaque assays.

EXAMPLE 7

Immunogenicity study

NIH-Swiss female outbred white mice, 3 to 4 weeks old were obtained from Harlan, Indianapolis, Ind. Four mice for each MRP$^R$ variant were inoculated with $10^3$ pfu virus by the i.p. route. Mice was sacrificed on day 15 post-inoculation and blood collected by cardiac puncture. The serum fraction was collected and stored at −20° C. Neutralization assays were performed as described in Wills et al. (1992).

EXAMPLE 8

Sequencing and analyzing the genome of virus RNAs

RT-PCR, cloning and sequencing virus RNA were as described before (Ni et al., 1994). Computer analyses of nucleic acid data and deduced amino acid sequences were accomplished using the MICROGENIE (Queen and Korn, 1984), PCGENE and Genetic Computer Group (Devereux et aL, 1984).

EXAMPLE 9

Generation and confirmation of MRP$^R$ variants

Japanese encephalitis virus strain P3 grown in C6–36 cells (P3/C6–36) was mixed and incubated with mouse brain, monkey brain or monkey liver membrane receptor preparations at 37° C. for 30 minutes, the mixture was pelleted and supernatant plaqued as described above. Japanese encephalitis P3 virus bound to mouse brain and monkey brain membrane receptor preparations but not monkey liver membrane receptor preparations (TABLE IV). P3/C6–36 virus bind to monkey brain membrane receptor preparations completely. For selection of mouse brain membrane receptor preparations resistant (MRP$^R$) variants, P3/C6–36 virus mixed with excess mouse brain membrane receptor preparations which resulted in a $10^{3.6}$ reduction in infectivity (TABLE V). Three plaques of P3 virus that escaped binding to the mouse brain membrane receptor preparations were selected and amplified in Vero cells.

TABLE III

P3 virus binding test to mouse brain, monkey brain and monkey liver membrane receptor preparations

|  | Infectivity (Log$_{10}$pfu)# | Binding index* | Binding (%) |
|---|---|---|---|
| Buffer | 6.1 | — | — |
| Mouse brain MRP | 2.5 | 3.6 | 99.97 |
| Monkey Brain MRP | >1.0 | >5.1 | >99.99 |
| Monkey liver MRP | 6.0 | 0.1 | 8.33 |

Infectivity: infectious virus remaining in supernatant following incubation of virus with MRP or buffer, and pelleting virus MRP complex as described above.
*binding index: $\log_{10}$ infectivity in buffer After plaque purification and amplification in Vero cells, all three MRP$^R$ variant viruses did not bind to fresh mouse brain membrane receptor preparations (TABLE V), which confirmed that they were true MRP$^R$ variants. In parallel, the P3/C6–36 virus used to generate the MRP$^R$ variants was also plaque purified and amplified in Vero cells (P3/Vero) for determination of effects of Vero cell passage on the phenotype P3 virus. This P3/Vero virus bound to mouse brain membrane receptor preparations with similar binding to P3/C6–36 virus (TABLE V).

TABLE IV

Confirmation that P3 virus mouse brain MRP$^R$ variants do not bind to mouse brain membrane receptor preparations (MRPs)

|  |  | Infectivity (Log$_{10}$ pfu) | | | |
|---|---|---|---|---|---|
| Virus Strain |  | Virus + Buffer | Virus + MB MRP | Binding index | Binding (%) |
| Parent | P3/C6-36 | 6.1 | 2.5 | 3.6 | 99.97 |
|  | P3/Vero | 7.3 | 3.6 | 3.7 | 99.98 |
| P3 Mouse Brain variants | MRP$^R$ I | 5.6 | 6.0 | -0.4 | NA |
|  | MRP$^R$ II | 6.0 | 6.6 | -0.6 | NA |
|  | MRP$^R$ III | 6.7 | 7.3 | -0.6 | NA |

NA: Not applicable.
MB MR: Mouse brain membrane receptor preparation
Binding index

EXAMPLE 10
Pathogenicity of wild-type JE virus strains P3 and its variants

Groups of outbred NIH-Swiss mice were inoculated by the i.c or i.p. route with either parental P3/C6–36 or P3/Vero virus, or one of the MRP$^R$ variants. The pfu/LD$_{50}$ values and AST±SEM were determined. Comparison of parental P3/C6–36 and P3/Vero viruses showed that plaque purification and amplification in Vero cells had little effect on the virulence of P3 virus in terms of both LD$_{50}$ following i.c. or i.p. inoculation (TABLE V) although P3/Vero virus was slightly less virulent than P3/C6–36 virus. In comparison, all three mouse brain MRP$^R$ variants were attenuated at least 200 fold compared with the parental P3 viruses following i.p. inoculation (i.e., neuroinvasiveness) (TABLE VI). Also, all three mouse brain MRP$^R$ variants were significantly attenuated in neurovirulence (at least 500 fold) compared with their parental viruses after i.c. inoculation of mice (TABLE II). The average survival times of mice infected with the mouse brain MRP$^R$ variants were also longer than that of the parental P3 virus (TABLE VII).

TABLE V

Mouse neurovirulence of parent JE P3/C6-36 or P3/Vero viruses and the mouse brain MRP$^R$ variants following intracerebral or intraperitoneal inoculation

|  |  | Route of inoculation | | |
|---|---|---|---|---|
|  |  | intraperitoneal | intracerebral | |
| Virus |  | pfu/LD$_{50}$ | pfu/LD$_{50}$ | AST ± SEM |
| Parent | P3/C3-36 | 50 | <0.0001 | 6.5 ± 0.3 |
|  | P3/Vero | 280 | 0.0004 | 6.0 ± 0.3 |
| Mouse brain Variants | MRP$^R$ I | >50,000 | 5.6 | 8.0 ± 1.2 |
|  | MRP$^R$ II | >50,000 | 0.8 | 8.0 ± 0.6 |
|  | MRP$^R$ III | >50,000 | 10.0 | 8.6 ± 1.0 |

: AST ± SEM: Average survival time ± standard error of the mean which were calculated from mice inoculated with 10 pfu virus by i.c. route.
*MRP$^R$ I/mouse brain: MRP$^R$ I virus infected mouse brain.
NT: not tested.

TABLE VI

Virus infectivity of JE virus parent P3 and its MRP$^R$ variants following i.c. or i.p. innoculation

|  |  | i.c. | | | | i.p. | | | |
|---|---|---|---|---|---|---|---|---|---|
|  |  | Day 2 | | Day 7 | | Day 2 | | Day 7 | |
| Inoculum |  | Brain | Sera | Brain | Sera | Brain | Sera | Brain | Sera |
| parent | P3/C3-36 | 6.4 ± 0.2* | 4.0 ± 0.3 | NA# | NA | <2.0 | 6.1 ± 0.9 | 3.4 ± 0.2 | 2.8 ± 1.0 |
|  | P3/Vero | 5.8 ± 0.2 | 2.9 ± 0.2 | NA | NA | <2.0 | 5.6 ± 0.5 | 2.9 ± 0.5 | 2.2 ± 0.1 |
| variants | MRP$^R$ I | 4.2 ± 0.5 | 2.0 ± 0.7 | 2.7 ± 0.9 | <2.0 | <2.0 | 3.0 ± 0.4 | <2.0 | 2.0 ± 0.3 |
|  | MRP$^R$ II | 4.6 ± 0.4 | <2.0 | 3.1 ± 0.3 | <2.0 | <2.0 | 4.6 ± 0.5 | <2.0 | 2.1 ± 0.6 |
|  | RP$^R$ III | 4.7 ± 0.1 | 2.0 ± 0.7 | 3.0 ± 0.6 | <2.0 | <2.0 | 2.9 ± 0.3 | <2.0 | <2.0 |

NA: not applicable due to mice died from infection
*infectivity expressed as $\log_{10}$ pfu/ml (mean ± S.E.M.), three mice per sample group.

TABLE VII

Neutralization antibody titre elicited by mouse brain MRP$^R$ escape virus variants

|  | MRP$^R$ I | MRP$^R$ II | MRP$^R$ III |
|---|---|---|---|
| Neutralization antibody titer | 320 | 320 | >320 |
|  | 160 | 160 | 320 |
|  | 160 | 160 | 160 |
|  | 40 | 160 | 160 |

Neutralization titer: Taken as the highest dilution of serum to neutralize 50% of homologous challenge virus.

EXAMPLE 11
Determination of infectivity of the MRP$^R$ variants following inoculation by the i.c. and i.p. routes Mice were sacrificed on days two and seven after i.c. inoculation of 1 pfu or i.p. inoculation of 1000 pfu of the viruses to determine whether or not the MRP$^R$ variants could replicate in the blood and brains of mice. All three mouse brain MRP$^R$ variants replicated in the infected mice (TABLE VIII). The infectivity of the MRP$^R$ variants in the brains and sera were lower than their parental virus at day two post i.c. inoculation. However, all mice inoculated by the i.c. route with parental P3 virus died by day seven post infection. The infectivity of the MRP$^R$ variants was significantly lower than parental virus in the sera at days two and seven post i.p. inoculation.

TABLE VIII

Comparison of amino acid changes in the E protein sequence of P3/C6-36 or P3/Vero and the mouse brain MRP$^R$ variants

| Position | P3/C6-36 | P3/Vero | MRP$^R$ mutants |
|---|---|---|---|
| E-46 | T | I | T |
| E-129 | A | T | T |
| E-209 | R | K | K |
| E-306 | G | G | E |
| E-351 | A | V | V |
| E-387 | E | G | G |
| E-408 | L | L | S |
| E-475 | A | A | A |

EXAMPLE 12
Immunogenicity of the MRP$^R$ variants

NIH-Swiss mice inoculated with the mouse brain MRP$^R$ variants induced neutralizing antibody in all infected mice by day 15 post i.p. inoculation (TABLE VII).

EXAMPLE 13
Comparison of nucleotide and amino acid sequence changes of the mouse and human brain MRP$^R$ variants with wild-type parent P3 viruses and P3 plaque purified and amplified in Vero cells To investigate the genetic differences and receptor attachment domain of parental P3 virus and its MRP$^R$ variants, the pre-memberane (prM), memberane (M) and evelope (E) protein genes of P3 viruses and the MRP$^R$ variants were cloned and sequenced. The P3/Vero virus had 13 nucleotide differences compared with the P3/C6–36 virus in prM, M and E protein genes (data not shown), which resulted in five amino acid changes at positions of E-46, E-129, E-209, E-351 and E-387 (TABLE VIII), which may be responsible for the reduced virulence of P3/Vero virus compared to P3/C6–36 virus. These amino acid differences can not be considered to be responsible for virus attenuation of the MRP$^R$ variants.

The three mouse brain MRP$^R$ variants had identical nucleotide sequences in prM, M and E protein genes. They had 23 nucleotide differences compared to the P3/C6–36 virus and 20 nucleotide differences to the P3/Vero virus (data not shown). However, these mouse brain MRP$^R$ variants have only two amino acid changes compared with parental P3/C6–36 and P3/Vero viruses at residues E-306 (G ->E) and E-408 (L ->S) (TABLE VIII).

EXAMPLE 14
Analysis of E protein secondary structures

Secondary structures of E protein of parental and the MRP$^R$ variants were analyzed at region around E-306 and E-408 by the Novotny and GGBSM program in PCGENE. The Novotny program revealed that charged residue profile, alpha helix propensity, beta sheet propensity and reverse turn propensity were changed when E-306 residue glycine mutated to glutamic acid, and hydrophobicity profile, alpha helix propensity, beta sheet propensity and reverse turn propensity were changed when E-408 residue leucine replaced by serine. The GGBSM program indicated that coil, extended and helical profile were changed when either residue E-306 (G<->E) or E-408 (L<->S) was changed (data not shown).

Virus binding to the host cell surface receptors is the first step in the virus replication cycle, and is directly involved in the tissue tropism and pathogenesis of many viruses (Fields & Greene, 1982). Despite their importance, the identities and host cell functions of relative few cell receptors for viruses are known or widely accepted. No cellular receptors for flaviviruses have been identified although it is assumed that E protein of flaviviruses plays a role in the cellular tropism by being involved in virus binding to cellular receptors. Recently, Chen et al. expressed E protein of dengue-2 virus which bound to Vero, CHO, endothelial, and glial cells. Recombinant E protein inhibited infection of Vero cells by dengue virus.

Investigation in vivo of cell receptor for viruses is difficult due to manipulation of animal tissues and the inability for most virus to purify sufficient virus to undertake physical binding assays. The present invention describes a procedure for selection of variants that could be generated by selection of virus that did not bind to membrane receptor preparations (MRPs) (TABLE II AND III). As a model, binding of Japanese encephalitis virus to mouse brain MRPs was examined. Specificity of the procedure was demonstrated by the inability of Japanese encephalitis virus to bind to monkey liver MRP (TABLE II) and the generation of variants was shown by the failure of mouse brain variants to bind to fresh mouse brain MRP. All three mouse brain MRP$^R$ variants were significantly attenuated for both neuroinvasiveness and neurovirulence compared with their wild-type parent P3 virus (TABLE IV). This suggests that selection of MRP$^R$ variants could be used as a novel approach to generate vaccine candidates.

Attenuation of the neurovirulence of the Japanese encephalitis P3 strain mouse brain MRP$^R$ variants may occur following selection of variants in the virus preparation that have mutated in the receptor attachment domain of the virus, which in the case of flaviviruses is the E protein. Such variants may have changed tissue tropism. Only two common amino acid substitutions were identified at residues E-306 and E-408 (TABLE VII). These two substitutions significantly changed secondary structure of E protein. Thus, these two amino acids play a critical role in attenuation of the mouse brain MRP$^R$ variants.

Involvement of E-306 in the attenuated phenotype is consistent with previous studies on the flaviviruses and confirmed the use of MRP to generate attenuated virus variants. Four other attenuated derivatives of wild-type Japanese encephalitis virus have been reported. Two groups reported monoclonal antibody neutralization resistant (MAb$^R$) variants that had mutation at E-270 and E-333 or E-52, E-363 and E-366. All of these variants had reduced mouse neuroinvasiveness but not neurovirulence to mouse. In comparison, the serials of live vaccines derived from SA14 virus have four E protein substitutions at E-138, E-176, E-315 and E-435. These vaccine are attenuated for both mouse neurovirulence and neuroinvasiveness in humans. Samiyoshi et al. (15) has suggested that the mutation at E-138 is a major determinant of attenuation of mouse neuorovirulence.

Mapping of the amino acid substitutions of above mutants and the mouse MRP$^R$ variants of the present invention onto the proposed model of the three dimensional structure of the E protein of the tick-born encephalitis (TBE) virus (Rey et al., 1995), a flavivirus related to Japanese encephalitis virus, revealed that many of the mutations cluster to domain three of E protein, suggests that the domain three is important in mouse virulence, probably as a virus attachment domain to the mouse cellular receptors. This is consistent with the proposal of Rey et al. (1995) and supported by studies of other flaviviruses which showed that MAb$^R$ variants to Louping ill virus (E-308, E-310 and E-311; Jiang et al., 1993; Gao et al., 1994), TBE virus (E-387) and dengue virus (E-383, E-384 and E-385; Hiramatsu et al., 1996; E-390, Sanchez et al., 1996) are all attenuated for mouse neurovirulence, and these mutations were mapped to domain III of the E protein.

The amino acid substitution at residue E-408 of the MRP variants is located in the stem region of the flavivirus E protein which links the ectodomain to the membrane anchor region. The transmembrane α helix stem region has recently been proposed as an important element for low-pH-induced oligonomic rearrangement of the E protein. The E-408 substitution alters the alpha-helix and virus induced membrane fusion.

TABLE II showed that neuroinvasiveness of the mouse brain MRP$^R$ variants was more attenuated than that of neurovirulence compared with their parents. The MRP$^R$ variants were found in the sera and but not in the brain at day two and day seven post-inoculation through i.p. route indicated that P3 virus variants may replicate in blood vessels but they have been difficult to penetrate the blood-brain barrier. The mechanism of attenuation of neuroinvasiveness of the mouse brain MRP$^R$ variants needs to be investigated further.

The present invention demonstrated that Japanese encephalitis virus mouse brain MRP$^R$ can be readily selected in vitro from parental virus seed in presence of excess amount of MRP. Selected virus MRP$^R$ variants have an attenuated phenotype in mouse. The present invention suggests that selection for MRP$^R$ variants from target tissue of the virus is one potential route to generate attenuated virus strains and that it is conceivable to generate attenuated variants with multiple mutations selection using MPRs from different tissues consecutively. Thus, the present invention provides a novel methodology permitting relatively cheap and rapid selection of the virus vaccine candidate(s).

TABLE IX

Membrane receptor variants of Yellow Fever virus and Langat virus

| Virus | Strain | MRP$ | Lethality'# |
|---|---|---|---|
| Yellow fever | FNV | — | 0.08 |
| | | MK-1 | >100 |
| | | MK-II | >100 |
| | | MK-IV | 80 |
| Langat | TP21 | — | 1.3 |
| | | HU-1 | 16 |
| | | MS, pH 7.0 | 16,000 |
| | | MS-II | <1000 |
| | | MS-I | 2000 |
| | | HU-III | 126 |

: lethality in 3–4 week old ice following intracerebral inoculation.
Figures are pfu/LD$_{50}$.
$: MRP = membrane receptor preparation,
MK: monkey brain,
MS: mouse brain,
HU: human brain.

TABLE X

Mouse neurovirulence following intracerebral and intraperitoneal inoculation of parent JE P3 virus grown in C6-36 or Vero cells and its mouse brain and human brain membrane receptor preparation escape (MRP$^R$)* variants

| | | Route of inoculation | | |
|---|---|---|---|---|
| Virus | | ip pfu/LD$_{50}$ | ic pfu/LD$_{50}$ | AST ± SEM$^\#$ |
| parent | C6-36 | 50 | <0.1 | 6.5 ± 0.3 |
| | Vero | 280 | 0.0004 | 6.0 ± 0.3 |
| Mouse | MRP$^R$ I | >50,000 | 5.6 | 8.0 ± 1.2 |
| brain | MRP$^R$ II | >50,000 | 0.8 | 8.0 ± 0.6 |
| Variants | MRP$^R$ III | >50,000 | 10.0 | 8.6 ± 1.0 |
| HBG[1] Variants | MRP$^R$ I | >5,000 | >100,000 | >14 |
| | MRP$^R$ II | >5,000 | >100,000 | >14 |
| HBW[2] variant | MRP$^R$ I | >5,000 | >100,000 | >14 |

[1]: HBG: human brain grey matter;
[2]: BGW: human brain white matter;
: AST ± SEM: average survival time ± standard error of the mean which were calculated from mice inoculated with 10 pfu virus by ic route;
*: MRP$^R$ I/mouse brain.
Virus recovered from mouse brain MRPR I virus-infected mouse brain;
ic: intracerebral;
ip: intraperitoneal.

TABLE X shows that the methodology of the present invention is not restricted to mouse brain MRPs. Human brain MRPs were used to generate MRP$^R$ s which were attenuated 5,000,000,000-fold for mouse neurovirulence. Moreover, the methodology is not restricted to Japanese encephalitis virus. Monkey brain MRP$^R$ variants of yellow fever virus were attenuated for mouse neurovirulence following intracerebral inoculation of weanling mice and mouse brain and human brain MRP$^R$ variants of Langat virus were attenuated for mouse neurovirulence following intracerebral inoculation of weanling mice.

The following references were cited herein:

Anderson, R., King, A. D. and Innis, B. L. 1992. Correlation of E proteins binding with cell susceptibility to dengue 4 virus infection. *J. Gen. Virol.* 73: 2155–2159.

Cao, J. X., Ni, H., Sil, B. K., Ryman, K. D., and Barrett, A.D.T. 1995.

Passage of Japanese encephalitis virus in HeLa cells results in mutations in the structural protein genes and attenuation of virulence in mice. *J. Gen. Virol.* 76: 2757–2764.

Cecilia, D. & Gould, E. A. 1991. Nucleotide changes responsible for loss of neuroinvasiveness in Japanese encephalitis virus neutralization-resistant mutants. *Virology* 181: 70–77.

Chen, Y., Maguire, T. and Marks, R. M. 1996. Demonstration of binding of dengue virus envelope protein to target cells. *J. Virol.* 70: 8765–8772.

Devereux J., Haeberli, P., and Smithies, 0. 1984. A comprehensive set of sequence analysis programs for the VAX. *Nucl. Acid. Res.* 12: 387–395.

Fields, B. N. and Greene, M.I. 1982. Genetic and molecular mechanisms of viral pathogenesis: implications for prevention and treatment. *Nature* 300: 19–23.

Gao, G. F., Hussain, M. H., Reid, H. W., and Gould, E. A. 1994. Identification of naturally occurring monoclonal antibody escape variants of louping ill virus. *J. Gen. Virol.* 75, 609–614.

Guirakhoo, F., Heinz, F.X., Mandl, C.W., Holzmann, H. & Kunz, C. 1991. Fusion activity of flaviviruses: comparison of mature and immature (prM-containing) tick-borne encephalitis virions. *J. Gen. Virol.* 72: 1323–1329.

Heinz, F.X., Auer, G., Stiasny, K., Holzmann, H., Mandl, C. Guirakhoo, F., and Kunz, C. 1994. The interactions of the flavivirus envelope proteins: implications for virus entry and release. *Arch. Virol.* 9: 339–348.

Hiramatsu, K., Tadano, M., Men, R. and Lai, C. J. 1996. Mutation analysis of a neutrolization epitope on the dengue type 2 virus envelope protein; Monoclonal antibody resistant DEN2/DEN4 chimeraes exhibit reduced mouse neurovirulence. *Virology* 224: 437–445.

Huang C. H. 1982. Studies of Japanese encephalitis in China. *Adv. Virol. Res.* 27: 71–101.

Ikmura, T. and Ohyama, A. 1988. Association between the pH-dependent conformational change of West Nile flavivirus E protein and virus-mediated membrane fusion. *J. Gen. Virol.* 69: 1247–1254.

Jiang, W. R., Lowe, A., Higgs, S., Reid, H., and Gould E. A. 1993. Single amino acid codon changes detected in louping ill virus antibody-resistance mutatants with reduced neurovirolence. *J. Gen. Virol.* 74, 931–935.

Lentz, T. L. 1990. The recognition event between virus and host cell receptor: a target for antiviral agents. *J. Gen. Virol.* 71: 751–766.

Middlemiss, D. N. and Frozard, J. R. 1983. 80 HDPAT discrimination between subtypes of 5-$HT_1$ recognition site. *Euro. J. Pharmacol.* 90: 151–153.

Mims, C. A. 1986. Virus receptors and cells tropism. *J. Infect.* 12: 199–203.

Monath, T. P. Ballinger, M. E., Miller, B. R. and Salaun, J. J. 1989. Detection of yellow fever viral RNA by nucleic acid hybridisation and viral antigen by immunochestry in fixed human liver. *American Journal of Tropical Medicine and Hygiene* 40: 663–668.

Monath, T. P. 1990. Flavivirus. p. 763–814. In *"Virology"*. B. N. Fields, D. M. Knipe, et al., eds. Raven press New York, Ni, H., Burns, N. J., Chang, G. J., Zhang, M. J., Wills. M. R., Trent, D. W., Sanders, P. G. and Barrett, A. D. T. 1994. Comparison of nucleotide and deduced amino acid sequence of the 5' non-coding region and structural protein genes of the wild-type Japanese encephalitis virus strain SA14 and its attenuated vaccine derivatives. *J. Gen. Virol.* 75: 1505–1510.

Olmsted, R. A., Baric, R. S., Sawyer, B. A. and Johnston, R. E. 1984. Sindbis virus mutants selected for rapid Growth in cell culture display attenuated virulence in animals. *Science* 225: 424–426.

Paulson, J. C. 1985. Interaction of animal viruses with cell surface receptors. Vol. 2, p. 131–219. In: *The receptors*, Edited by Conn, P.M. Orlando: Academic Press.

Rey, F. A., Heinz, F. X., Mandl, C., Kunz, C & Harrison, S. C. 1995. The envelope glycoprotein from tick-borne encephalitis virus at 2 A resolution. *Nature* 375: 291–298.

Sanchez I. J., & Ruiz B. H. 1996. A single nucleotide change in the E protein of dengue 2 Mexican strain affects neurovirulence in mice. *J. Gen. Virol.* 77: 2541–2545.

Stiasny, K. Allison, S. L., Marchler-Bauer, A., Kunz, C. and Heinz F. X. 1996. Structural requirements for low-pH-induced rearrangements in the E protein glycoprotein of tick-borne encephalitis virus. *J. Virol.* 70: 8142–8147.

Sumiyoshi, H., Hoke, C. H. & Trent, D. W. 1992. Infectious Japanese encephalitis virus RNA can be synthesized from in vitro cDNA templates. *J. Virol.* 66: 5425–5431.

Westway, E. G., Brinton, M. A., Gaidamovich, S. Y., Horzinek, M. C., Igarashi, A., Kaarianen, L., Lvov, D. K., Portfield, J. S., Russell, P. K. and Trent, D. W. (1985). Flaviviradae. *Intervirology* 24: 183–192.

Wills, M. R., Sil, B. K., Cao, J. X. and Barrett, A. D. T. 1992. Antigenic characterization of the live attenuated Japanese encephalitis vaccine virus SA14–14–2: a comparison with isolates of virus covering a wild geographic area. *Vaccine* 10: 861–872

Yu, Y. X., Wu, P. F., Ao, J., Liu L. H. and Li H. M. 1981. Selection of a better immunogenic and highly attenuated live vaccine virus strain of Japanese Encephalitis. I. Some biological characteristics of SA14–14–2 mutant. Chinese *J. Microbiol. Immunol.* 1: 77–84

Yu, Y. X., Zhang, G. M., G., Y. P., Ao, J. and Li H. M. 1988. Safety of a live attenuated Japanese Encephalitis virus vaccine (SA14–14–2) for children. *Am. J. Trop. Med. Hyg.* 39: 214–217

The following publications were cited by reference to numbers.

1. Tsai TF, Yu YX. Japanese encephalitis vaccines. In: Plotkin SA, Mortimer EA Jr, eds. Vaccines. 2nd ed. Philadelphia: WB Saunders, 1995: 671–713
2. Ni et al., *J Gen Virol* 1996;77:1449–1455.
3. Eckels et al.,*Vaccine* 1988;6:513–518
4. Aihara et al.,*Virus Genes* 1991; 5:95–109.
5. Nitayaphan et al.,*Virology* 1990; 177: 541–552.
6. Ni et al., *J Gen Virol* 1994;75:1505–1510.
7. Ni et al., *J Gen Virol* 1995;76:409–413.
8. Chen et al., *Am J Trop Med Hyg* 1982;31:403407.
9. Hase et al., *Arch Virol* 1993;130:131–143.
10. Hasegawa et al.,*Virology* 1992; 191:158–165.
11. Cecilia et al.,*Virolo~y* 1991; 181:70–77.
12. McMinn et al., *Virology* 1995; 211:10–20.
13. Jiang et al., *J Gen Virol* 1993;74:931–935.
14. Holzmann et al., *J Virol* 1990;64:5156–5159.
15. Sumiyoshi et al., *J Inf Dis* 1995; 171:1144–51.
16. Chen et al., *Virology* 1996; 223: 79–88.
17. Rey et al., *Nature* 1995;375:291–298.
18. Jan et al., *J Gen Virol* 1995;76:573–580.
19. Falgout et al., *JVirol* 1993; 67:2034–2042.
20. Wallner et al., *J Gen Virol* 1996;77:1035–1042.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of selecting virus vaccine candidates by selecting virus variants that do not bind to brain membrane receptor preparations, comprising the steps of:
    (a) preparing a brain membrane receptor preparation;
    (b) mixing an amount of a virus of interest with an amount of said membrane receptor preparation containing excess membrane receptors to form a virus-membrane receptor preparation suspension;
    (c) centrifuging said suspension to form a supernatant;
    (d) determining residual virus infectivity in said supernatant; and
    (e) isolating individual membrane receptor preparation binding-resistant virus variants which are useful as virus vaccine candidates.

2. The method of claim 1, wherein said brain membranes are selected from the group consisting of mouse brain membranes, monkey brain membranes and human brain membranes.

3. The method of claim 1, wherein said brain membrane receptor preparation has a protein concentration of about 20–40 mg wet brain per ml.

4. The method of claim 1, wherein said residual virus infectivity in said supernatant is determined by infecting a cell monolayer and counting plaques produced.

5. The method of claim 1, wherein said the individual membrane receptor preparation binding-resistant variant plaques and the viruses are amplified.

6. The method of claim 1, wherein said variants generated are incubated with fresh brain membrane receptor preparations and a lack of binding of the variants to fresh brain membrane receptor preparations confirm that the variants are true variants.

7. The method of claim 1, wherein said variants are attenuated for neuroinvasiveness and neurovirulence.

8. The method of claim 1, wherein said virus is selected from the group consisting of yellow fever, Japanese encephalitis, dengue-4 and langat.

* * * * *

UNITED STATES PATENT AND TRADEMARK OFFICE
CERTIFICATE OF CORRECTION

PATENT NO. : 6,010,894
DATED : January 4, 2000
INVENTOR(S) : Alan Barrett, Haolin Ni and Kate Ryman It is certified that error appears in the above-identified patent and that said Letters Patent is hereby corrected as shown below:

Title page,
The figure should be labeled -- Figure 1 --.

Column 2,
Lines 23-24, please remove the paragraph indention, making line 24 in the same paragraph as line 23.

Column 3,
Line 67, "are" should read -- area --.

Column 4,
Line 6, "are" should read -- area --.

Column 5,
Line 21, under Table II "intracerebral" should be moved to the right, until it is above "AST±SEM#" in line 22.
Line 33, please insert the word -- the -- between the words "of" and "Yale".

Column 6,
Line 47, "aL, 1984)" should read -- al, 1984) --.

Column 7, Table III,
Line 10, "Monkey Brain MRP" should read -- Monkey brain MRP --.

Column 8, Table V,
Line 28, please underline "intraperitoneal".

Column 8, Table VI,
Line 1, "applicable due to" should read -- applicable because --.

Column 9,
Line 57, should read -- pre-membrane (prM), membrane (M) and envelope (E) --.

Column 11,
Line 13, "has" should read -- have --.

Column 12, Table IX,
Line 5, "Lethality'#" should read -- Lethality # --.
Line 7, "MK-1" should read -- MK-I --.
Line 8, "MK-11" should read -- MK-II --.

UNITED STATES PATENT AND TRADEMARK OFFICE
CERTIFICATE OF CORRECTION

PATENT NO. : 6,010,894
DATED : January 4, 2000
INVENTOR(S) : Alan Barrett, Haolin Ni and Kate Ryman It is certified that error appears in the above-identified patent and that said Letters Patent is hereby corrected as shown below:

Column 12,
Line 49, "MRP$^R$ s" should read -- MRP$^R$s --.

Column 13,
Lines 52-53, "*American Journal of Tropical Medicine and Hygiene*" should read -- *Am. J. of Trop. Med. Hyg.* --.
Line 55, "press" should read -- Press --.
Line 67, "Science" should read -- *Science* --.

Column 14,
Line 2, "*receptors*" should read -- *Receptors* --.
Line 29, "Chinese" should be italicized.
Line 38, "Vaccines" should be italicized.
Lines 44 and 45, "*J Gen Virol*" should read -- *J. Gen. Virol.* --.
Line 46, "*Am J Trop Med Hyg*" should read -- *Am. J. Trop. Med. Hyg.* --.
Line 47, "*Arch Virol*" should read -- *Arch. Virol.* --.
Line 49, "*Virolo~y*" should read -- *Virology* --.
Line 51, "*J Gen Virol*" should read -- *J. Gen. Virol.* --.
Line 52, "*J Virol*" should read -- *J. Virol.* --.
Line 53, "*J Inf Dis*" should read -- *J. Inf. Dis.* --.
Line 56, "*J Gen Virol*" should read -- *J. Gen. Virol.* --.
Line 57, "*J Virol*" should read -- *J. Virol.* --.
Line 58, "*J Gen Virol*" should read -- *J. Gen. Virol.* --.

Signed and Sealed this

Thirteenth Day of November, 2001

Attest:

NICHOLAS P. GODICI
*Attesting Officer*    Acting Director of the United States Patent and Trademark Office